United States Patent [19]

Tremmel et al.

[11] Patent Number: 5,171,538

[45] Date of Patent: Dec. 15, 1992

[54] REAGENT SUPPLY SYSTEM FOR A MEDICAL ANALYTICAL INSTRUMENT

[75] Inventors: Ewald Tremmel, Waldsee; Erich Weiss, Mannheim; Thomas Simon, Bürstadt; Kurt-Lutz Elste, Erzhausen, all of Fed. Rep. of Germany

[73] Assignee: Boehringer Mannheim GmbH, Mannheim, Fed. Rep. of Germany

[21] Appl. No.: 616,038

[22] Filed: Nov. 20, 1990

[30] Foreign Application Priority Data

Nov. 21, 1989 [DE] Fed. Rep. of Germany ....... 3938559

[51] Int. Cl.⁵ ............................................. B01L 3/02
[52] U.S. Cl. .................................... 422/100; 422/102; 73/863.85; 73/864.74; 73/864.85; 73/864.86
[58] Field of Search ................ 422/100, 102, 67, 68.1, 422/63; 215/1 C, 6, 10; 73/863.85, 864.85, 864.86, 864.87, 864.74, 863.32

[56] References Cited

U.S. PATENT DOCUMENTS

| 2,776,076 | 1/1957 | Nunn | 222/83.5 |
|---|---|---|---|
| 3,647,386 | 3/1972 | Gilford | 422/102 |
| 3,924,471 | 12/1975 | Singer | 73/421 |
| 4,126,418 | 11/1978 | Krasnow | 422/64 |
| 4,387,076 | 6/1983 | Cabrera et al. | 422/67 |
| 4,764,342 | 8/1988 | Kelln et al. | 422/72 |
| 4,785,948 | 11/1988 | Strassheimer | 215/1 C |
| 4,865,211 | 9/1989 | Hollingsworth | 215/1 C |
| 4,901,878 | 2/1990 | Humphries | 215/1 C |
| 4,923,098 | 5/1990 | Schoonover et al. | 215/1 C |
| 4,976,925 | 12/1990 | Porcher et al. | 422/100 |

FOREIGN PATENT DOCUMENTS

| 0252632 | 1/1988 | European Pat. Off. . |
|---|---|---|
| 0287900 | 10/1988 | European Pat. Off. . |
| 2112991 | 9/1972 | Fed. Rep. of Germany . |
| 2217669 | 10/1973 | Fed. Rep. of Germany . |
| 2002218 | 9/1974 | Fed. Rep. of Germany . |
| 2414196 | 10/1975 | Fed. Rep. of Germany . |
| 3042333A1 | 6/1982 | Fed. Rep. of Germany . |
| 3237999A1 | 4/1983 | Fed. Rep. of Germany . |
| 3515824A1 | 11/1985 | Fed. Rep. of Germany . |
| 0221315 | 9/1986 | Fed. Rep. of Germany . |
| WO83/00932 | 3/1983 | Int'l Pat. Institute . |

OTHER PUBLICATIONS

The Condensed Chemical Dictionary-10th edition, G. G. Hawley 1981, p. 1026.

Primary Examiner—James C. Housel
Assistant Examiner—Maureen M. Wallenhorst
Attorney, Agent, or Firm—Nikaido, Marmelstein, Murray & Oram

[57] ABSTRACT

A reagent supply system for a medical anlytical instrument includes a reagent space provided on the instrument and reagent vessels which are received in the reagent space. In the reagent space there is provided at least one reagent vessel compartment with a bottom, lateral guide elements, and a top guiding element, as well as a front stop. The instrument contains a fluid communication system for connection with a reagent vessel situated in the reagent vessel compartment. On the end face of the reagent vessel compartment is disposed a hollow needle near the bottom surface thereof and extending in a direction which is parallel to the bottom surface. The reagent vessel has on its front wall facing the end face a pierceable seal with a pierceable elastic stopper.

17 Claims, 2 Drawing Sheets

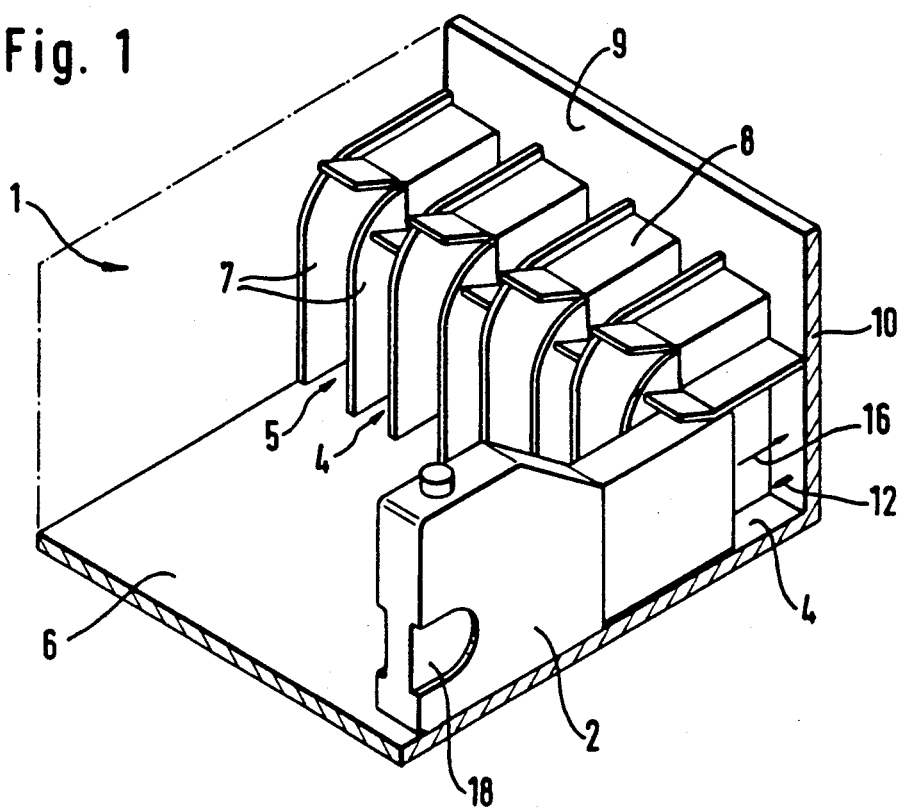
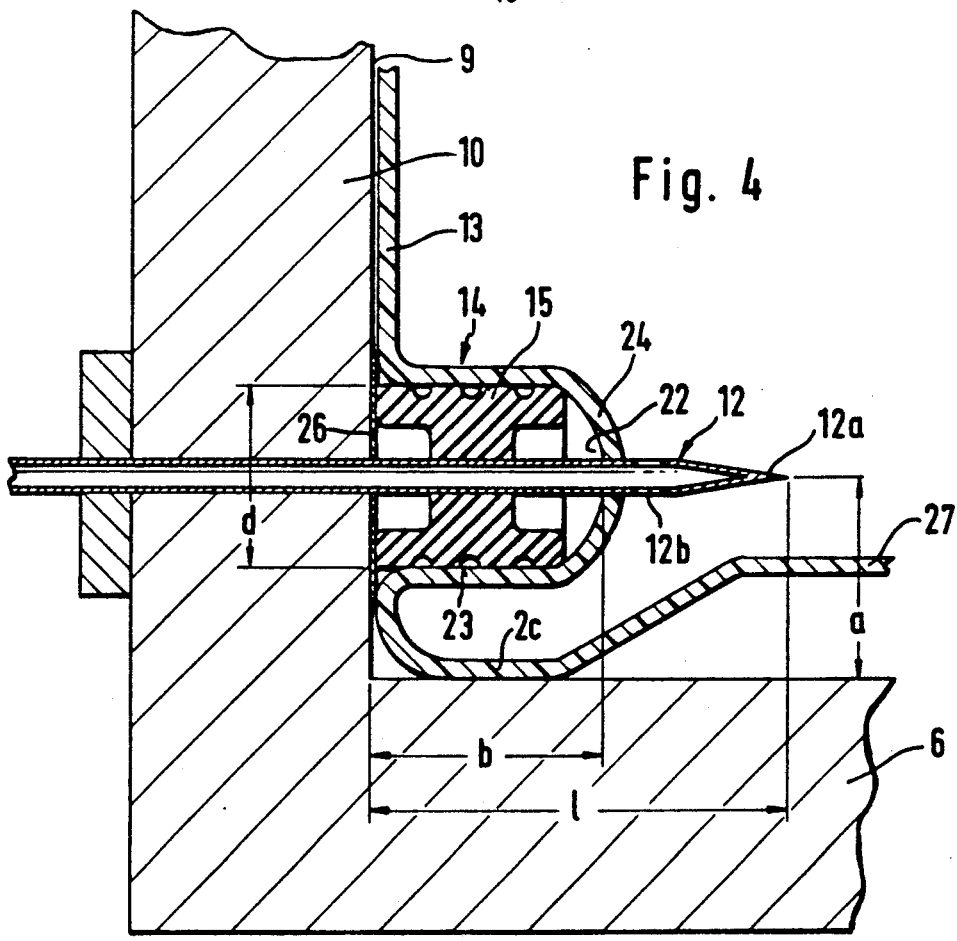

REAGENT SUPPLY SYSTEM FOR A MEDICAL ANALYTICAL INSTRUMENT

BACKGROUND OF THE INVENTION

The present invention relates to a reagent supply system for a medical analytical instrument.

Medical analytical instruments in the sense of the present invention serve to examine body fluids, especially blood. Modern instruments of this kind are largely fully automatic in operation, only the samples still having to be inserted in appropriate sample vessels and the desired analyses entered.

The invention is intended for instruments which operate with liquid reagents which are contained in reagent vessels of plastic. The instruments usually have a cooled reagent space. The reagents are transported in the instrument from the reagent vessels to the reaction vessels and there mixed with the sample, and after completion of the reaction a physically detectable change (usually a colouring) is measured as a measure of the analysis. The reagent vessels are frequently specially adapted to the reagent space of a particular instrument. By this means particularly space-saving accommodation and effective cooling of the reagents is possible. Reagent vessels and the reagent space of the instrument belonging to them, if they are functionally adapted to each other, form a system which is here called a reagent supply system.

For the transport of the reagents from the reagent vessel into the reaction vessel essentially two basically different techniques are used, namely the pipetting technique and the dispenser technique.

In the pipetting technique a pipette, usually fastened to a movable arm, dips from above through the open reagent vessel, and an appropriate amount of reagent is sucked in and transferred in the pipette (which is also known as a transfer needle) to the reaction vessel. This technique makes it possible o change the reagent vessels easily. A complicated instrument mechanism is however required. Also the transfer of reagents is relatively slow, as a result of which the throughput rate of the instrument is limited.

With the dispenser technique the reagent vessels are permanently connected individually by a line to the instrument. The connection lines are a part of a line system through which the reagents are supplied in a suitable manner (which is of no importance for the present invention) to the reaction vessels and thereby to the analysis. By this means, with relatively little mechanical complication, they are always available. This allows high analysis frequencies and thereby very rapidly operating automatic, analysers.

The dispenser technique has however considerable disadvantages with regard to handling. Usually flexible connecting tubes are introduced from above into the reagent vessels so that they end just above the vessel bottom. This is difficult and can easily lead to errors. In particular it can occur that air is sucked in if the flexible tubes do not dip deeply enough into the reagent. Also when the flexible tubes are interchanged they must each time be washed in cleaning liquid in order to prevent the transfer of reagent, especially if as is often customary—various reactions are carried out in the same channel of the instrument and accordingly different reagents are led through one flexible tube.

SUMMARY OF THE INVENTION

The above and other objects are accomplished according to the invention in that, with the object of simplifying the handling of the medical analytical instrument as described in the foregoing especially when interchanging the reagent vessels, in the reagent space at least one reagent vessel compartment is provided with a bottom, lateral and top guiding elements, and a front stop, and wherein on the front of the reagent vessel compartment a hollow needle is disposed near the bottom and running parallel to it, and wherein the reagent vessel has a pierceable seal with a pierceable elastic stopper in its front wall facing the end face.

Pierceable seals are known for other uses, for example infusion vessels or implantable vascular connections (so-called "ports"). The use of this technique for reagent supply systems of medical analytical instruments has, however, been precluded by the special requirements which have to be taken into consideration in this field, which have been surmounted by the present invention. These include the following points in particular:

The reagents are stored in the reagent vessels for a very long time (sometimes several years). They sometimes contain very reactive chemical compounds which must be completely free from environmental influences during storage and which attack numerous materials.

Many of the reagents used in medical analysis are very expensive. Any connection system must therefore be so arranged that as small as possible a residual volume remains in the vessel.

The analytical instruments should as far as possible be capable of being operated by less well trained staff, and the quality of the analysis must not suffer thereby.

The reagent space is cooled, temperatures of 2° to 3° C. being not uncommon in the area of its walls.

The invention satisfies these requirements to a very high degree, particularly when the especially preferred measures described below are used individually or in combination with each other.

With regard to the stability to storage of the reagents, it proves to be especially advantageous if the reagent vessel of plastic has an uninterrupted wall in the area of the pierceable seal, which is pierced together with the pierceable seal by the hollow needle. The pierceable seal is therefore preferably located in a blind hole closed to the internal space of the reagent vessel. In this connection it is advantageous if the hollow needle is not—as otherwise usual—ground obliquely at the end, but has a closed point and a lateral opening behind the point. By this means the pierced-out part of the vessel wall is reliably prevented from entering the hollow needle. Titanium has proved to be a particularly suitable reagent-resistant material for the hollow needle.

With a view to obtaining the smallest possible residual volume of reagent (dead volume) it is essential that the hollow needle runs near the bottom of the reagent vessel compartment. Accordingly on the vessel the distance between the central axis of the pierceable seal and the reagent vessel bottom is preferably smaller than 1 cm. This in turn determines a small diameter of the pierceable stopper of preferably less than 1 cm. In order to achieve a reliable seal with such a small diameter, according to another preferred embodiment an unusually soft elastomer with a Shore hardness of less than 50 is used for the pierceable stopper. This should be relatively long in shape, a cylindrical flask stopper, whose length exceeds its diameter, being especially preferred.

With a view to simple operation it is essential that the reagent vessel compartment be so designed that when the hollow needle is stuck into the pierceable seal the reagent vessels are guided from every side so that the hollow needle exactly hits the centre of the pierceable seal. The lateral and top guiding elements of the reagent holder compartment in conjunction with its bottom serve for that purpose. A front stop, which optionally can also be provided on the hollow needle itself, limits the penetration movement. Such a guidance from every angle is already used in some known instruments in order to position the reagent vessels. The expert cannot, however, derive any indications from this of the possibility of using a pierceable seal.

The invention will be described in greater detail below with reference to an embodiment which is illustrated in the drawings.

BRIEF DESCRIPTION OF THE DRAWINGS

FIG. 1 is a perspective view of a reagent supply system according to the invention;

FIG. 4 is an enlarged, side sectional view of a portion of the system of FIG. 2 wherein the hollow needle of FIG. 3 penetrates a pierceable seal.

DETAILED DESCRIPTION OF THE PREFERRED EMBODIMENT

Figure 2:
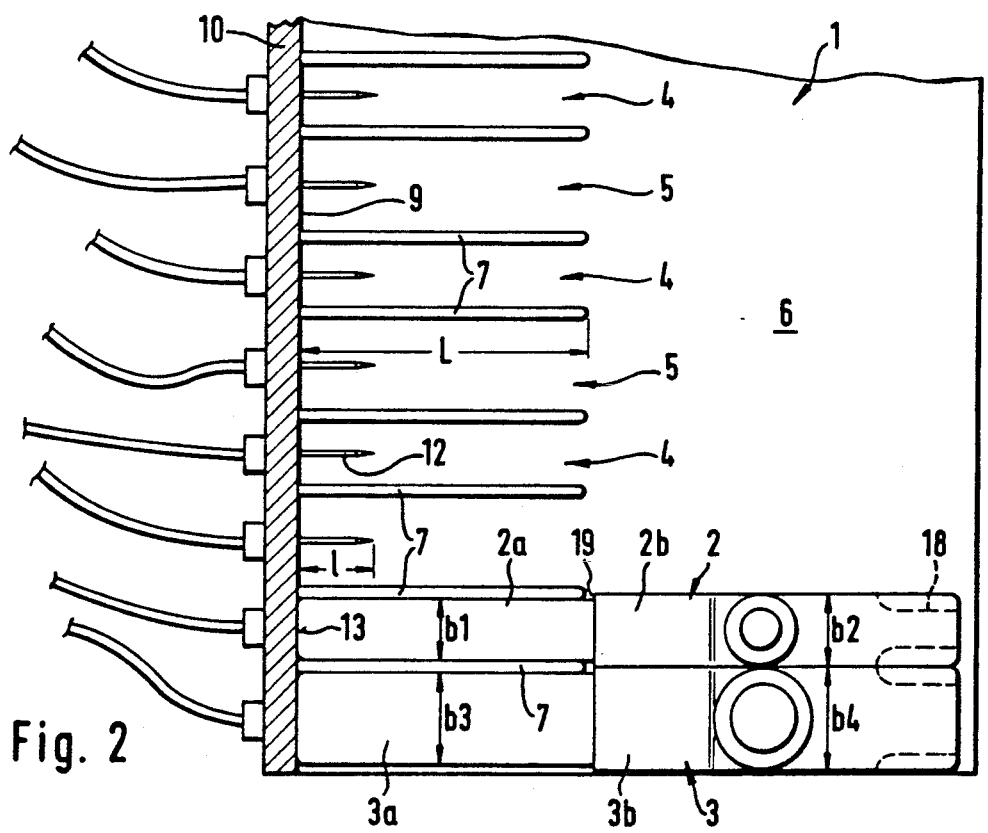
FIG. 2 is a top sectional view of a reagent supply system in accordance with FIG. 1, with top guiding elements removed.

A reagent supply system is shown in FIGS. 1-4, and includes a reagent space 1, which is part of an analytical instrument which is not shown, and reagent vessels 2 and 3. The reagent vessels 2 and 3 in the present case are intended to have two different reagent volumes of, for example, 300 ml and 600 ml respectively, and accordingly the reagent vessels 2 and 3 have different widths as shown in FIG. 2. The reagent space 1 has partitions 7 dividing the reagent space 1 into a plurality of compartments 4 and 5, the compartments 4 and 5 having two different widths to accomodate the widths of the reagent vessels 2 and 3, respectively.

Each of the reagent vessel compartments 4 and 5 has a base formed by a portion of a bottom surface 6, lateral guiding elements formed by the partitions 7, top guiding elements 8, and a front stop is provided by a back wall 10 of the reagent space. In the case shown, the reagent space bottom 6 is common to all of the compartments 4 and 5. The partitions 7 serve as the lateral guiding elements, and the top guiding elements 8 are preferably formed from angle sheet iron members which are fastened to the partitions 7. The back wall 10 of the reagent space 1 serves as the front stop for stopping forward movement of front walls 13 of the reagent vessels 2 and 3 (i.e., the back wall 10 limits further movement of the vessels 2 and 3 in the direction of introduction of the vessels 2 and 3).

A hollow needle 12 is provided at a front end surface 9, formed by the back wall 10, of each reagent vessel compartment, near the reagent space bottom 6. The needle 12 has a longitudinal axis which extends in a direction which is substantially parallel to the reagent space bottom 6. The needle 12 includes a point 12a and at least one lateral opening 12b; as shown in FIG. 4, the needle 12 has a pair of opposed lateral openings 12b.

Figure 3:
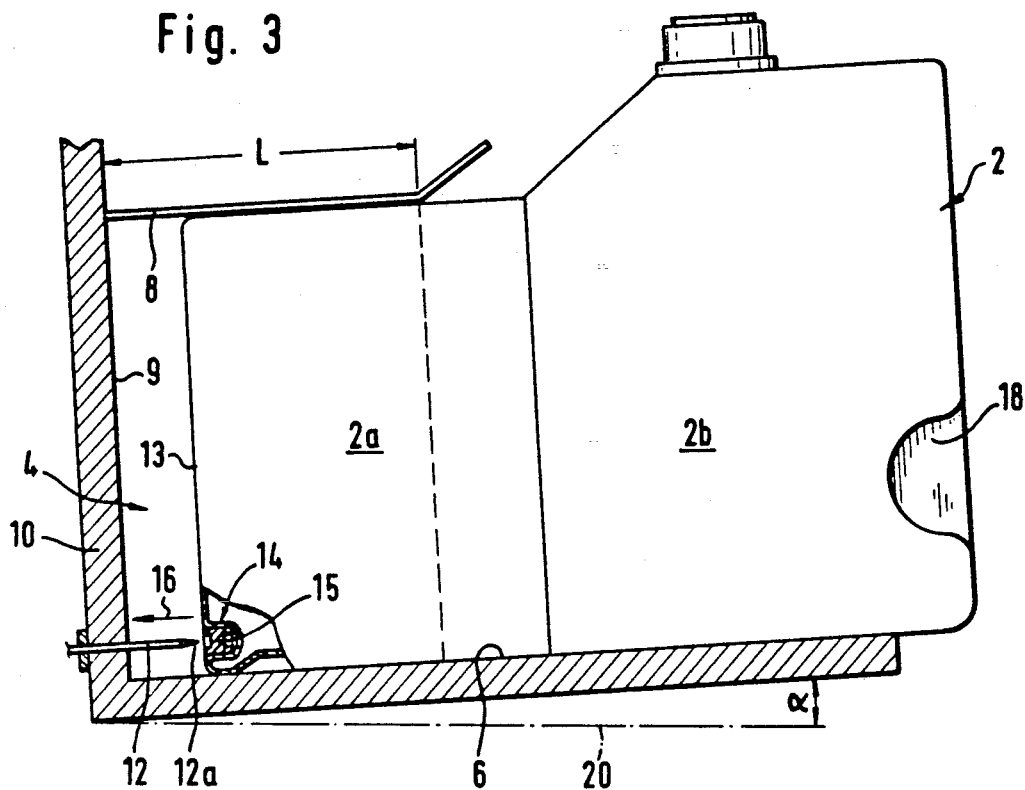
FIG. 3 is a side sectional view of the system according to FIG. 1, in which a reagent vessel is in a position before penetration by a hollow needle.

As shown in FIGS. 2-4, each of the reagent vessels 2 and 3 have a front wall 13. A pierceable seal 14 is disposed in the front wall 13, and includes a pierceable elastic stopper 15.

In use, a reagent vessel 2 or 3 is pushed into the appropriate one of the reagent vessel compartments 4 and 5 in a direction towards the front end surface 9 (i.e., the direction indicated by arrow 16 in 3). Then, in the last part of the movement during the insertion process, the reagent vessel 2 or 3 is guided by the reagent space bottom 6, the partitions 7, and the top guiding element 8, such that the center of the pierceable seal 14 contacts the point 12a of the hollow needle 12. In the case shown, the back wall 10 of the reagent space 1 forms a stop against further movement of the vessel 2 or 3 in the insertion direction indicated by the arrow 16. The length L shown in FIG. 2 over which the reagent vessels 2 and 3 are guided during their insertion in the insertion direction (indicated by the arrow 16), must be greater than the effective length 1, also shown in FIG. 2, by which the hollow needles 12 project into the reagent space 1 from the front end surface 9.

The reagent vessels 2, 3 are preferably elongated in shape, and have a length which is preferably at least five times their width. This not only makes a space-saving accommodation possible, but also reduces the dead volume which would otherwise be necessarily present in the bottoms of the vessels 2 and 3.

In the preferred embodiment, the following relationships apply and are substantially as shown in the drawings, however it will be understood that the present invention is not limited to the specific dimensions shown, and can have other proportions. First, respective front vessel sections 2a and 3a, which adjoin the respective front walls 13 of the vessels 2 and 3, have smaller widths b1, b3, respectively, than do respective rear vessel sections 2b, 3b which respective widths b2, b4, as shown in FIG. 2. In addition, the widths b1, b3 of the front vessel section 2a, 3a, respectively, are preferably smaller than the widths b2, b4, respectively, by the space required by the partitions 7. Generally speaking, the widths b2, b4 of the vessels in the second, rear vessel sections 2b, 3b are such that, when the reagent vessels 2 and 3 are inserted into the reagent vessel compartments 4, 5 (such that the reagent vessels 2 and 3 are disposed immediately side by side), the rear vessel sections 2b, 3b of the adjacent reagent vessels 2, 3 are in direct contact with each other.

Recessed grips are additionally provided on the rear vessel sections 2b, 3b. These recessed grips 18 are molded such that they are recessed toward the interior. In this way, a space-saving arrangement is obtained. Furthermore, good cooling can be achieved in the cooled reagent space by this arrangement. Both the front vessel sections 2a, 3a and rear vessel sections 2b, 3b preferably have essentially rectangular bases, as shown in the drawings, the width increasing at a transition region 19.

It is preferred that, as shown in FIG. 3, the reagent space bottom 6 of the reagent compartments 4, 5 be inclined relative to the horizontal (dotted line 20) towards the front end surface 9 by an angle a, which should be in a range of about 2 degrees to 5 degrees. This inclination makes an important contribution to reducing the dead volume in the containers 2 and 3 as they are emptied, since the liquid in them will flow toward the region of the needle 12.

FIG. 4 shows details of the preferred embodiment of the pierceable seal 14, a vessel wall 2c in the region of the pierceable seal, and the hollow needle 12. It can be seen that in the front wall 13 of the vessel 2, a blind hole 22 is provided as the socket for the pierceable stopper 15, the blind hole 22 having a cylindrical wall 23 and an end portion 24. In order to ensure a sufficiently large uniform wall thickness of the vessels 2 and 3, it is advantageous if, as shown, the end portion 24 is curved so as to have a dome shape which is convex toward the interior of the reagent vessel 2 or 3, and has a smooth transitional region with the cylindrical wall 23 of the blind hole 22. The point 12a of the hollow needle is conical and closed. The lateral opening 12b is provided behind the point 12a of the needle 12 for drawing in of the reagent liquid in the respective one of the vessels 2 and 3.

The pierceable stopper 15, in the form of a flask stopper in the case shown in FIG. 4, is covered with a sealing film 26, which in the area of the pierceable seal 14 is fastened to the front wall 13 of the reagent vessel 2. In this way, the stopper 15 is protected from sliding out when the vessel 2 is removed from the respective one of the reagent vessel compartments 4 and 5. The sealing film 26 also forms an additional seal for sealing the liquid in the vessels 2 and 3.

According to the invention, the same reagent vessel 2, 3 can be repeatedly penetrated by and removed from the hollow needle 12, without leaking of the pierceable seal 14.

Furthermore, the wall 2c of the vessel 2 is curved inwardly in the region of the vessel bottom 27 towards the interior of the vessel 2. In this way also the dead volume is reduced.

Altogether, according to the invention, it is possible by combination of the aforementioned measures to limit the dead volume in the vessels 2 and 3 to less than 5 ml. In order to ensure this, the relatively complicated vessel shape, as shown in FIG. 4, is required. This vessel shape can, however, be produced relatively efficiently and relatively inexpensively in an extrusion blow-molding process from HDPE (high density polyethylene). In this form the preferred embodiment has the following dimensions. A distance a between the vessel wall 2c and the center of the pierceable seal 14 is equal to 8 mm. A depth b of the blind hole 22 is equal to 9.5 mm. A diameter d of the blind hole 22 is equal to 7 mm. The effective length l of the needle 12 is approximately 17 mm. The present invention is not limited to these dimensions, however.

It will be understood that the above description of the present invention is susceptible to various modifications, changes and adaptations, and the same are intended to be comprehended within the meaning and range of equivalents of the appended claims.

What is claimed is:

1. A reagent supply system for a medical analytical instrument which utilizes reagents for performing medical analysis, said reagent supply system comprising:
   a reagent space in the medical analytical instrument, said reagent space being stationary with respect to said medical analytical instrument and for accommodating a plurality of reagent vessels;
   a plurality of reagent vessels which can be received in said reagent space;
   a plurality of reagent vessel compartments in said reagent space for receiving a portion of each of said reagent vessels, each of said plurality of reagent vessel compartments having a base, and lateral guiding elements for slidably receiving a reagent vessel such that said reagent vessel is guided thereby in a direction parallel to said base, and
   a reagent communication system provided in the medical analytical instrument for communicating reagent fluid from the plurality of reagent vessels, said reagent communication system having a connection means for establishing fluid communication with the interior of a reagent vessel disposed in a reagent vessel compartment, such that a reagent contained within said reagent vessel can be withdrawn by said reagent communication system, said reagent communication system including a plurality of stationary hollow needles, each of said needles being fixedly disposed on a front end of each of said reagent vessel compartments near said base, and having a longitudinal needle axis extending substantially parallel to said base, each of said reagent vessel compartments having at least one of said plurality of needles disposed therein, said at least one needle being stationary with respect to said reagent vessel compartment; and
   each of said reagent vessels having a pierceable seal in a front wall thereof, said pierceable seal comprising a pierceable elastic stopper which can be penetrated by one of said hollow needles to establish fluid communication with said interior of said reagent vessel,
   wherein said reagent vessels may be pushed in an insertion direction parallel to said base of said reagent vessel compartments and are guided in said insertion direction for a length which is greater than an effective length of said hollow needles.

2. A reagent supply system according to claim 1, wherein said pierceable seal includes a socket formed by said front wall of said reagent vessels, said socket comprising a blind hole closed against the interior of said reagent vessels.

3. A reagent supply system according to claim 2, wherein said blind hole has a dome-shaped curved bottom, being convex toward said interior of said reagent vessels, said blind hole has a cylindrical side wall, and said blind hole also has a relatively smooth-shaped transitional region between said convex bottom and said cylindrical side wall of said blind hole.

4. A reagent supply system according to claim 1, wherein the distance of a center region of said pierceable seal from a bottom of said reagent vessels is less than 1 cm.

5. A reagent supply system according to claim 1, wherein said pierceable seal has a diameter of less than 1 cm.

6. A reagent supply system according to claim 1, wherein said pierceable elastic stopper is formed from an elastomer with a Shore hardness of less than 50.

7. A reagent supply system according to claim 1, wherein said pierceable elastic stopper has the form of a cylindrical flask stopper having a length which exceeds its diameter.

8. A reagent supply system according to claim 1, wherein a sealing film is fastened to said front wall of said reagent vessels in the region of said pierceable seal covering said pierceable seal.

9. A reagent supply system according to claim 1, wherein a bottom of said reagent vessels is curved inwardly toward said interior of said reagent vessels.

10. A reagent supply system according to claim 1, wherein each of said reagent vessels have an elongated shape, such that a length of each reagent vessel is at least five times a width thereof.

11. A reagent supply system according to claim 10, wherein
said reagent space includes a plurality of said reagent vessel compartments, disposed immediately side by side, for the reception of a plurality of reagent vessels,
a width of adjacent ones of said reagent vessels, in a front vessel section of each of said plurality of reagent vessels is smaller than the width of respective rear vessel sections of respective ones of said plurality of reagent vessels, said width of said front vessel sections being defined by a width of said front wall of the respective reagent vessels; and
a width of respective ones of said plurality of reagent vessels at respective said rear vessel sections with respect to the width of the lateral guiding elements of said reagent vessel compartments is such that said rear vessel sections of adjacent ones of said plurality of reagent vessels are in direct contact with each other.

12. A reagent supply system according to claim 11, wherein each of said hollow needles have a closed point and behind said point a lateral opening.

13. A reagent supply system according to claim 12, wherein each of said hollow needles consist of titanium.

14. A reagent supply system according to claim 1, wherein said base of said reagent vessel compartments is inclined towards said front end thereof, wherein the insertion direction is correspondingly inclined.

15. A reagent supply system according to claim 11, further comprising grip portions on each of said rear vessel sections.

16. A reagent supply system according to claim 10, wherein said reagent space includes a plurality of said reagent vessel compartments disposed side by side for the reception of a respective plurality of reagent vessels.

17. A reagent supply system according to claim 1, further comprising a stop portion on said front end of each of said reagent vessel compartments for stopping further movement of said reagent vessels in the insertion direction.

* * * * *